(12) United States Patent
De Ferra et al.

(10) Patent No.: US 6,444,822 B1
(45) Date of Patent: Sep. 3, 2002

(54) PROCESS FOR THE PREPARATION OF 3-SUBSTITUTED 4-PHENYL-PIPERIDINE DERIVATIVE

(75) Inventors: Lorenzo De Ferra; Pietro Massardo, both of Rome; Oreste Piccolo, Sirtori; Giorgio Cignarella, Milan, all of (IT)

(73) Assignee: Chemi S.p.A., Patrica (IT)

( * ) Notice: Subject to any disclaimer, the term of this patent is extended or adjusted under 35 U.S.C. 154(b) by 0 days.

(21) Appl. No.: 09/627,689

(22) Filed: Jul. 28, 2000

(30) Foreign Application Priority Data

Aug. 2, 1999 (IT) .......................... MI99A1731

(51) Int. Cl.⁷ .................. C07D 405/12; C07D 211/40
(52) U.S. Cl. ................ 546/197; 546/216; 546/240
(58) Field of Search ................... 546/197, 216, 546/240

(56) References Cited

U.S. PATENT DOCUMENTS

| 4,007,196 A | | 2/1977 | Andres | |
| 5,258,517 A | * | 11/1993 | Zepp et al. | 546/240 |
| 6,051,712 A | * | 4/2000 | Binggeli et al. | 546/194 |

FOREIGN PATENT DOCUMENTS

| EP | 0190496 | | 8/1986 |
| EP | 0223334 | | 5/1987 |
| EP | 374674 | * | 6/1990 |
| EP | 374675 | * | 6/1990 |
| WO | WO 9636636 | | 11/1996 |
| WO | WO98/01424 | * | 1/1998 |
| WO | WO98/53824 | * | 12/1998 |

OTHER PUBLICATIONS

Surrey "Name reactions in Organic Chemistry" Aca. Press. pp. 173–174 (1961).*
Waldmann et al. "Amino acid esters as chiral auxiliaries in asymmetric cycloadditions" CA 115:159693 (1991).*
Aparicio et al. "N–amino–2–pyridones from acetohydrazide derivatives" J. Chem. Soc. Perkin. Trans. I, pp. 1975–1979 (1989).*

* cited by examiner

*Primary Examiner*—Celia Chang
(74) *Attorney, Agent, or Firm*—Hedman & Costigan, P.C.

(57) ABSTRACT

Described herein is the process for the preparation of 3-substituted 4-phenyl-piperidine derivatives of formula (I)

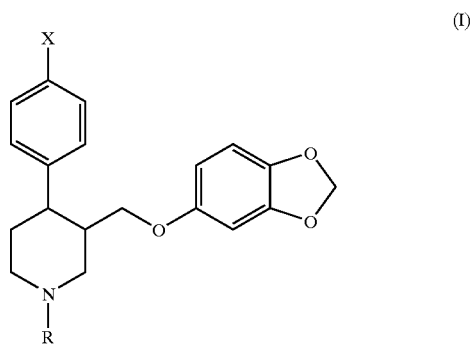

(I)

in which X is selected from H and F, and R is selected from the group consisting of H, C1–C6 alkyl, C3–C6 alkenyl, and benzyl, comprising three steps starting from the monoamide of malonic acid and cinnamic aldehyde, or derivatives thereof.

9 Claims, 1 Drawing Sheet

PROCESS FOR THE PREPARATION OF 3-SUBSTITUTED 4-PHENYL-PIPERIDINE DERIVATIVE

FIELD OF INVENTION

The present invention concerns a process for the preparation of 3-substituted 4-phenyl-piperidine derivatives of formula (I) given below, in particular for the preparation of paroxetine.

STATE OF THE ART

Paroxetine, i.e. the 3-[(1,³-benzodioxol-5-yloxi)methyl]-4-(p-fluoro-phenyl)piperidine, is a compound capable of acting as an inhibitor of serotonin's recaptation at the synaptic junctions and, due to its pharmacological properties, has been used for a long time as an effective antidepressant.

The paroxetine molecule has two chiral centres at positions 3 and 4 of the piperidine ring, and therefore possesses various enantiomeric forms: the (−) trans isomer having the absolute configurations (3S,4R) is pharmacologically the most active one for paroxetine.

Therefore numerous preparation procedures for paroxetine and its precursors have been developed up to present, and separation processes of the racemic mixtures obtained have been studied, so as to isolate the pharmacologically most active isomer.

The U.S. Pat. No. 4,007,196 (Ferrosan AS) concerns, for example, 3-substituted 4-phenyl-piperidine derivatives of formula (A)

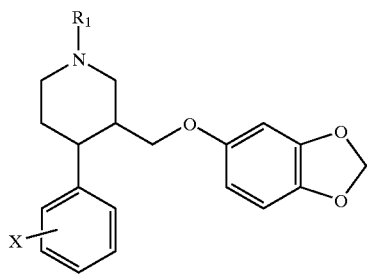

(A)

among which the paroxetine is also included, when X=p-fluoro and $R_1$=H. Moreover, the preparation procedure of such compounds is described starting from the corresponding carbinols prepared, in their turn, by reduction of the formula B) compounds

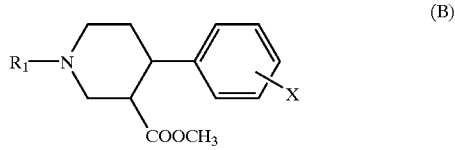

(B)

with a metallic complex hydride, for example lithium aluminum hydride. The formula (B) compounds are prepared starting from methyl arecoline (1,2,5,6-tetrahydro-3-pyridincarboxylate) or suitable homologues thereof, by reaction with X-phenyl-magnesium bromide; such compounds (B) are obtained as a cis/trans mixture in which each isomer has, in its turn, two enantiomeric forms.

The procedure according to the U.S. Pat. No. 4,007,196 therefore provides that resolution methods of the racemic mixtures are used to obtain the pharmacologically most active optic isomer, i.e. the (−)trans isomer, having the absolute configuration (3S,4R).

Such a preparation process involves considerable drawbacks, such as the lack of stereoselectivity and the use as the starting compound of arecoline, a highly toxic and expensive reagent.

The European Patent EP 223334 (Beecham Group PLC) describes a process for the preparation of 4-(4'-fluorophenyl)-3-hydroxymethyl-1-methyl-piperidine by reduction of formula a) compounds a)

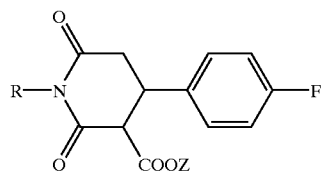

in which Z is alkyl and R is H, alkyl or arylalkyl.

According to EP 223334 the compounds of formula a) are prepared by the reaction of alkyl amido-malonates with suitable cinnamic acid esters, e.g. alkyl or aryl esters. From this reaction an enantiomeric mixture is thus obtained; to gain a pharmaceutically useful end product, it is therefore necessary to perform the resolution of the mixture and isolate the pharmacologically most active enantiomer.

The European Patent Application EP 812827 (Sumika Fine Chemicals Co.) describes a process for the preparation of 4-(4'-fluorophenyl)-3-hydroxymethylpiperidine in the (−) trans isomer form by reduction of (−)trans-2-keto-4-(4'-fluorophenyl)-5-carboxy-piperidine, obtained by the resolution of the corresponding racemic mixture, or by reduction of 2-keto-4-(4-fluorophenyl)-5-carboxyalkyl-piperidine in the racemic form, and the subsequent resolution of 3-hydroxymethyl-piperidine thus obtained.

It is apparent how the above described processes involve a considerable number of steps which is automatically reflected in a low overall yield of the synthesis. It is therefore felt necessary to set up a preparation process of 3-substituted 4-phenyl-piperidine derivatives, and in particular of paroxetine, that does not present the drawbacks experienced with the known processes as described above.

SUMMARY OF THE INVENTION

Now the Applicant has surprisingly found that it is possible to obtain the 3-substituted 4-phenyl-piperidine derivatives of formula (I) reported below, in particular paroxetine, starting from commercially available raw materials and by few synthetic steps of easy industrial scalability.

Therefore the subject of the present invention is a process for the preparation of formula (I) 3-substituted 4-phenyl-piperidine derivatives

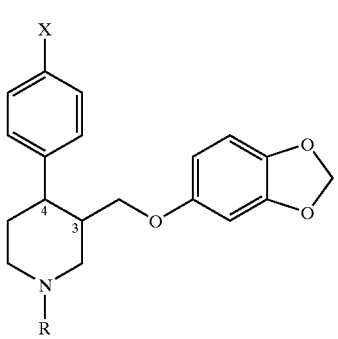

(I)

in which X is selected from H and F, and R is selected from the group consisting of H, C1–C6 alkyl, C3–C6 alkenyl, and benzyl, comprising the following steps:

a) Michael addition between the formula (II) cinnamic aldehyde and the amide of formula (III) in which $R_1$ is selected from the group consisting of C1–C6 alkyl, C3–C6 alkenyl, and benzyl, to obtain the formula (IV) 2-keto-3-carboxyalkyl-4-phenyl-6-hydroxy-piperidine, optionally enriched in the (3S,4R) isomer by using a suitable chiral catalyst:

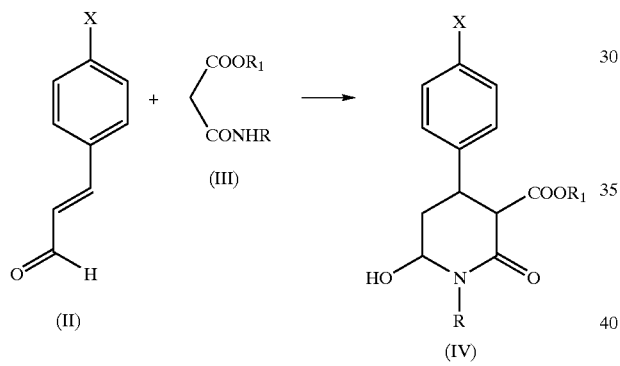

b) reduction of the formula (IV) 2-keto-3-carboxyalkyl-4-phenyl-6-hydroxy-piperidine coming from step a) to obtain the 3-hydroxymethyl4-phenyl-piperidine of formula (V):

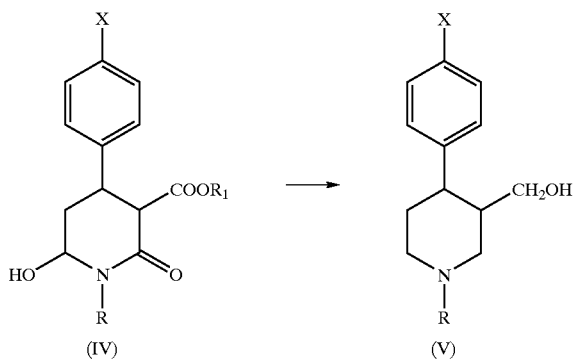

c) reaction of 3-hydroxymethyl-4-phenyl-piperidine of formula (V) coming from step b) with sesamol (VI) to obtain the formula (I) 3-[(1,3-benzodioxol-5-yloxi)methyl-]4-phenyl-piperidine:

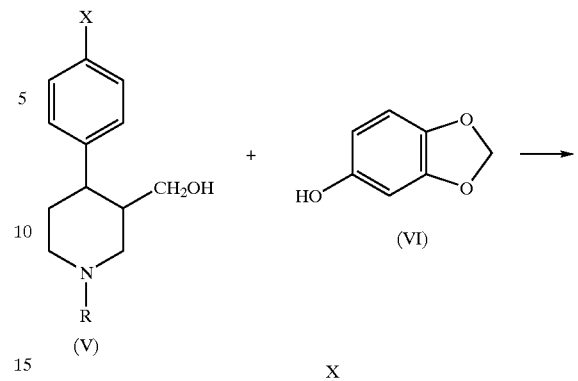

The intermediate of formula (IV) reported above represents a further subject of the invention.

The characteristics and advantages of the process according to the present invention will be illustrated in detail in the following description.

DETAILED DESCRIPTION OF THE INVENTION

Figure 1:
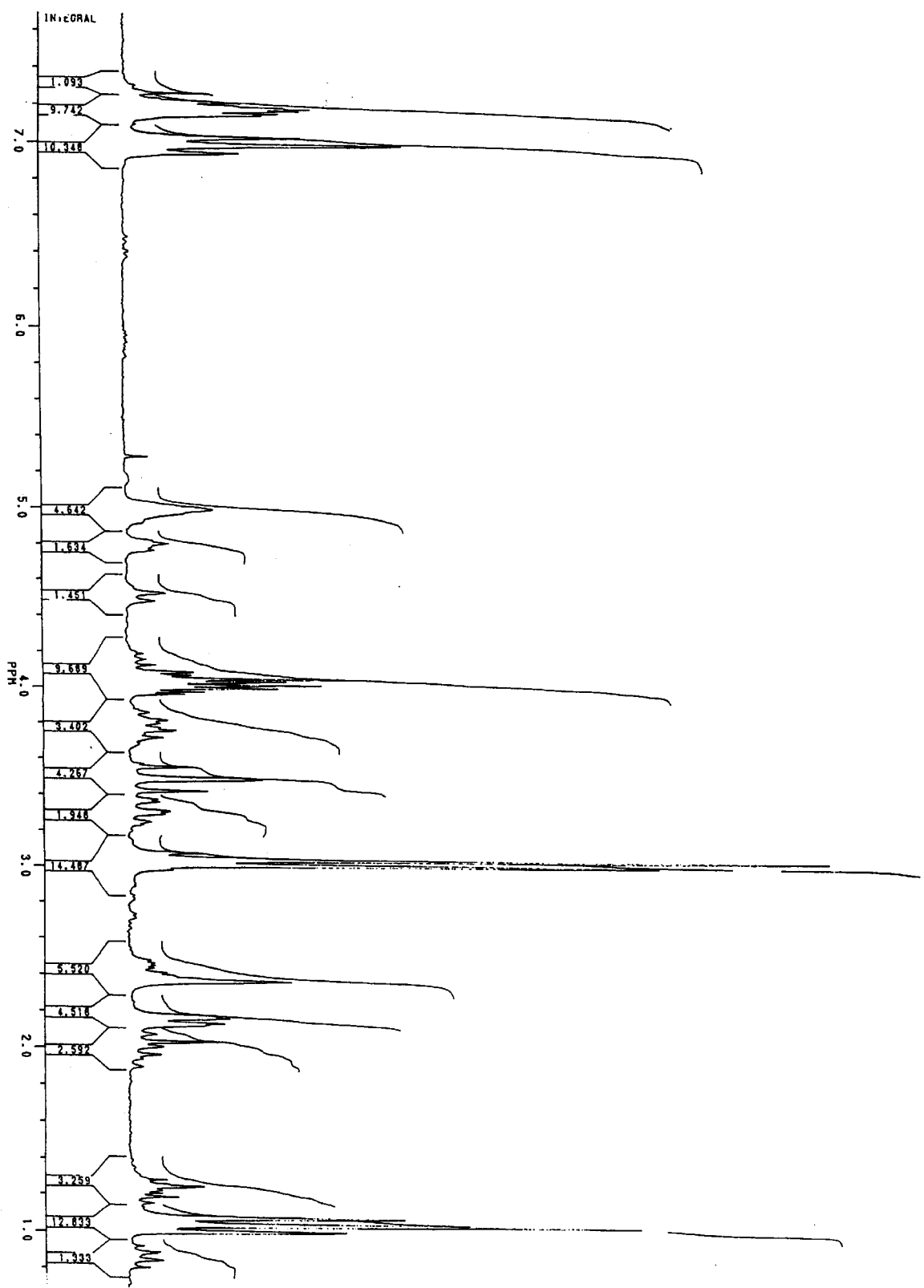
FIG. 1: $^1$H-NMR spectrum (Bruker 200 MHz; $CDCl_3$) of the 2-keto-3-carboxyethyl-4-(p-fluorophenyl)-6-hydroxy-piperidine of formula (IV) obtained as described in Example 14.

The present compounds of formula (II), (III) and (VI) are products which are commercially available, or may be easily prepared starting from products available on the market by using simple known procedures.

According to a particular embodiment of the present invention, the addition reaction between the cinnamic aldehyde of formula (II) and the formula (III) amide is carried out in step a) in the presence of a salt of (L)-proline, preferably in the presence of (L)-proline potassium salt or (L)-proline rubidium salt, by using as the solvent an organic solvent selected from the group consisting of aromatic solvents, chlorinated solvents, esters, ethers, hydrocarbons, nitriles and amides.

Preferably the molar ratio between the (L)-proline salt and the cinnamic aldehyde of formula (II) ranges between 0.05:1 and 1:1.

A particular advantage of the invention is the fact that the present step a) allows the attainment of the formula (IV) 2-keto-3-carboxyalkyl-4-phenyl-6-hydroxy-piperidine completely in the trans isomer form having a configuration of the carbon atom at position 4 which is mainly R.

Apart from the product of formula (IV), the dehydration products thereof may be obtained in step a), but the subsequent reduction in step b) also leads them to the formation of the formula (V) compounds.

In the case R=H, the dehydration product which may be obtained in step a) is the following compound of formula (IV'):

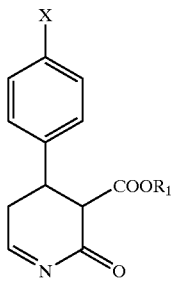

(IV')

Such compound (IV') is a further subject of the present invention.

The reduction of 2-keto-3-carboxyalkyl-4-phenyl-6-hydroxy-piperidine of formula (IV) obtained in step a) may be carried out in the present step b) by the means of the commonly used reducing systems, e.g. with hydrides such as $LiAlH_4$, or $NaBH_4$ in combination with acids, or with diborane.

According to a preferred embodiment of the present process, step b) is carried out by using lithium aluminium hydride as the reducing agent.

According to the present process, the reaction step c) between the formula (V) compound and the sesamol (VI) is preferably carried out with triphenylphosphine in the presence of diethyl azodicarboxylate under Mitsunobu's reaction conditions.

The 3-[(1,3-benzodioxol-5-yloxi)methyl]-4-phenyl-piperidine (I) coming from step c), when R≠H, may be transformed into the corresponding compound where R=H by means of different known processes depending on the nature of group R; for example, when R=benzyl, such a group may be removed by catalytic hydrogenation whereas, when R=alkyl, the corresponding compound with R=H may be obtained by reaction with phenyl chloroformiate.

Otherwise, still starting from the formula (III) compounds in which R≠H, a product of formula (I) in which R=H may be anyhow obtained by removing the R group from the formula (V) compound coming from step b), before subjecting it to the final step c), following known procedures, of hydrogenation when R is benzyl, of dealkylation when R is an alkyl group, and deallylation when R is an alkylene group.

The following examples are provided for illustrative, non limiting purposes of the present invention.

EXAMPLE 1

Preparation of the Formula (III) Amide in Which R is Methyl and $R_1$ is Ethyl

A solution prepared by dissolving 6 g of ethylmalonyl chloride (0.039 mol) in 5.5 ml of tetrahydrofuran (THF) is added, drop by drop and under stirring, to 40 ml of a 2M solution of methylamine (0.080 mol) in THF, cooled to 0° C. During the addition, care is taken of keeping the temperature at 0–5° C. After addition, the reaction mixture is kept under stirring at room temperature for 12 hours.

After having filtered the reaction mixture to eliminate the formed salts, the organic phase is evaporated, thus leaving an oily residue that is purified by flash chromatography using a 98:2 methylene chloride: methanol mixture as the eluant. 5 g of pure product are obtained, which proves to be the monoamide of malonic acid (III), with an 89% yield.

EXAMPLE 2

Preparation of Formula (IV) 2-keto-3-carboxyalkyl-4-4-phenyl-6-hydroxy-piperidine in Which R is Methyl. $R_1$ is Ethyl and X is H To a 100 ml twin-neck flask containing 12 ml of chloroform are added, in succession and in Ar atmosphere, 1.54 g (11.65 mmol) of cinnamic aldehyde, 1.69 g (11.65 mmol) of the monoamide prepared as described in Example 1, and 0.233 g (1.165 mmol) of (L)-proline rubidium salt.

The resulting mixture is kept under stirring at 20–22° C. for 12 hours. The pH is adjusted to around 5 with 2N HCl, afterwards the organic phase is separated, then washed with water and dried on anhydrous sodium sulphate.

The residual solvent is evaporated and the oil obtained is purified by flash chromatography using silica gel as stationary phase and the mixture methylene chloride: ethyl acetate 95:5 as the eluant.

2.5 g of an orange oil are obtained, which by NMR analysis proves to be the title product, with a 76% yield.

EXAMPLE 3

Preparation of Formula (V) 3-hydroxymethyl-4-phenyl-piperidine in Which R is Methyl and X is H A suspension obtained with 0.68 g (18.04 mmol) of $LiAlH_4$ and 20 ml of anhydrous THF and cooled to 0° C. is put in a 100 ml flask.

To this suspension is added, drop by drop in 10 minutes, a solution obtained by dissolving in 10 ml of anhydrous THF 1 g (3.6 mmol) of 2-keto-3-carboxyethyl-4-phenyl-6-hydroxy-piperidine prepared as described in Example 2.

After addition, the temperature is brought up to room temperature, and the mixture is then heated to 30–35° C. keeping the reaction mixture at this temperature for 4 hours.

After having cooled to 0° C., 10 ml of ethyl acetate, 0.5 ml of methanol and 0.5 ml of water are added, drop by drop and in succession, to the reaction mixture.

The formed salts are eliminated by Buchner filtration, then washing with methanol. The filtrate is then dried on anhydrous sodium sulphate, and the solvent is evaporated to obtain 0.8 g of an oily residue which is purified by flash chromatography using silica gel as the stationary phase and the mixture methylene chloride: methanol 95:5 as the eluant.

0.48 g of a white solid are obtained, that by NMR analysis proves to be the title product (yield=65%; m.p.=85–87° C).

HPLC analysis on Chiralpak AD Column with the mixture hexane 95, isopropanol 5, diethylamine 0.1 as the eluant, shows that the isomers (3S,4R) and (3R,4S) are in the ratio of 70:30.

EXAMPLE 4

Preparation of Formula (V) 3-hydroxymethyl-4-phenyl-piperidine in Which R is Methyl and X is H 5 g (18 mmol) of 2-keto-3-carboxyethyl4-phenyl-6-hydroxy-piperidine prepared as described in Example 2 are put in a flask together with 25 ml of THF.

4 g of sodium borohydride are added, then the mixture is cooled to 0° C., and a solution obtained by dissolving 4.7 g (35.2 mmol) of aluminium chloride in 30 ml of THF is added in 30 minutes and under stirring. The reaction mixture is heated up to 40° C., and left at this temperature for 16 hours under stirring.

The temperature is then brought to 20° C., and 28 ml of a 15% HCl aqueous solution is added; after addition the reaction mixture is heated to 65° C. and kept at this temperature for 2 hours. A basic pH is reached by addition of a 30% aqueous solution of sodium hydroxide, then 10 ml of water are added and the organic phase is separated.

By evaporation of the solvent 4.62 g of a residue are obtained, that the NMR analysis proves to be N-methyl-3-hydroxymethyl-4-phenyl-piperidine with a purity of 71% (Purity by HPLC 71%, Yield 89%).

EXAMPLE 5

Preparation of Formula (V) (3S, 4R)-3-hydroxymethyl-4-phenyl-piperidine in Which R is Methyl and X is H 4 g of sodium borohydride and 100 ml of dimethoxyethane are put in a reactor. After cooling to 0° C., 16.8 g of a 23% HCl solution in dimethoxyethane are added. Keeping the temperature below 5° C. a solution, obtained by dissolving in 30 ml of dimethoxyethane 5 g (18 mmol) of 2-keto-3-carboxyethyl-4-phenyl-6-hydroxy-piperidine prepared as described in Example 2, is added under stirring.

After addition, the temperature is increased to 35° C., and the reaction mixture is left to react at this temperature under stirring for 18 hours. 40 ml of a 32% HCl aqueous solution are added together with 40 ml of water, and the mixture is left under stirring for 20 minutes.

A pH=10 is reached by the addition of sodium carbonate, afterwards the dimethoxyethane is removed at reduced pressure and the reaction product is extracted with methylene chloride (150 ml×2). From the resulting two organic phases collected together, 3.7 g of a residue are obtained by solvent evaporation; by NMR analysis such residue proves to be N-methyl-3-hydroxymethyl-4-phenyl-piperidine (Purity by HPLC 82%, Yield=82%).

Resolution: 3.5 g of the so obtained product were dissolved in 18 ml of acetone. To this solution 6.6 g (-Di-O-O'-p-toluyl-L-tartaric acid dissolved in 45 ml acetone were added. Temperature was raised to 50° C., then the mixture was cooled to 0° C. The product was collect by filtration obtaining, after drying, 5.3 g of the resolved salt that was then converted into the free base, yielding 1.75 g of the (3S, 4R) pure isomer (HPLC analysis).

EXAMPLE 6

Preparation of Formula (I) (3S, 4R)-3-[1,3-benzodioxol-5-yloxi)methyl]-4-phenyl-piperidine in Which R is Methyl and X is H 1.37 g (5 mmol) of (3S, 4R)-N-methyl-3-hydroxymethyl-4-phenyl-piperidine prepared according to Example 5 are put in a flask together with 0.7 g (5 mmol) of sesamol and 1.95 g (7.5 mmol) of triphenylphosphine in 6 ml of THF; 1 ml of diethyl azodicarboxylate is then added in 2 minutes and under stirring. The mixture is left to react at room temperature for 12 hours.

Upon completion of the reaction, 6 ml of toluene and 10 ml of water are added, adjusting the pH to 4–5 by adding HCl. The two phases are separated by collecting the aqueous phase. A second extraction with water is carried out, adjusting the pH to 4–5 with HCl, and the aqueous phase is added to the previous one.

From the so obtained aqueous portion the reaction product is extracted with methylene chloride, adjusting the pH to 11 by addition of a 30% sodium hydroxide aqueous solution.

2.64 g of a brown oil are obtained by evaporation to dryness of the organic phase. This product is purified by crystallisation, dissolving it in a hot mixture of methanol (6.5 ml) and water (2.5 ml), then cooling it to 0° C. obtaining 0.89 g of title product (Yield 52%).

EXAMPLE 7

Preparation of Formula (I) (3S, 4R)-3-[1,3-benzodioxol-5-yloxi)methyl]-4-phenyl-piperidine in Which R=X=H 15 g (46.3 mmol) of (3S, 4R)-3-[1,3-benzodioxol-5-yloxi)methyl]-4-phenyl-piperidine of formula (I), obtained as described in Example 6, are dissolved in a flask with 200 ml of methylene chloride, then 10 g of phenyl chloroformiate are added under stirring. The mixture thus obtained is refluxed, maintaining both temperature and stirring for 6 hours. The mixture is then cooled to 25° C. and two extractions with water are performed, the first with 200 ml and the second one with 100 ml of water. The organic portion is concentrated and then taken up with 100 ml of Methyl Cellosolve®.

After having added 15 g of potassium hydroxide (flakes; titre=85%) it is refluxed, keeping under reflux for 3 hours. The solvent is then evaporated at reduced pressure, and the residue thus obtained is suspended in 200 ml of water.

Acetic acid is added under stirring up to pH 10, then 400 ml of ethyl acetate are added and the two portions are left to separate; the organic portion is washed with 100 ml of water and then concentrated until a residual volume of 150 ml is reached. 3 g of acetic acid are added, and cooled to 0° C. Afterwards, the product is isolated by filtration, obtaining 8.1 g of desfluoro paroxetine acetate (yield=47.5%).

EXAMPLE 8

Preparation of Cinnamic Aldehyde of Formula (II) in Which X is F 40 g (0.303 mol) of p-fluoro-benzaldehyde, 40 g of acetaldehyde, 20 ml of ethanol and 20 ml of water are put in a reactor.

A solution obtained by dissolving 0.8 g of sodium hydroxide in 3.6 ml of ethanol and 3.6 ml of water is added over 1 hour to the reaction mixture, which is kept under stirring at a temperature lower than 30° C. The reaction mixture is then kept at room temperature for 3 hours, then acidified up to pH 5 with HCl and concentrated at reduced pressure until its volume is halved. The reaction product is extracted with 100 ml of toluene, then the solvent is removed and the product is isolated by distillation (T=90° C. and p=2 mmHg). In this way 25 g of p-fluoro-cinnamaldehyde are obtained, with a yield of 54.6%.

EXAMPLE 9

Preparation of the Formula (II) Amide in Which R is Benzyl and $R_1$ is Ethyl A solution of 15 g ethoxycarbonyl acetyl chloride in 100 ml methylene chloride is added at 5° C. to a solution of 21 g benzyl amine in 100 ml methylene chloride. The mixture is kept under stirring for 3 hours at 5° C. benzylamine hydrochloride is filtered off, the solution is washed twice with hydrochloric acid 2% and the product purified by chromatography on silica gel using the mixture THF:n-heptane 1:1 as the eluant. After evaporation of the solvent from the homogeneous fractions the weight of the so obtained 2-carboethoxy-N-benzyl-acetamide is 19.8 g (yield 90%).

EXAMPLE 10

Preparation of the Formula (IV) 2-keto-3-carboxyalkyl-4-phenyl-6-hydroxy-piperidine in Which R is Benzyl, $R_1$ is Ethyl and X is F A solution is prepared by dissolving in 46 ml of toluene 12.07 g of 2-carboethoxy-N-benzyl-acetamide obtained as described in Example 9 and 8.36 g of the p-fluorocinnamaldehyde obtained as described in Example 8, and heated to 70° C.

A solution of 0.305 g L-proline and 0.29 ml rubidium hydroxide 50% in water is added under stirring in 20 minutes. Temperature and stirring are maintained for 4 hours. 15 ml water are added and, after having separated the organic phase, solvent is removed at reduced pressure.

The residue (15.4 g; yield 76%) is used without purification in the subsequent step.

EXAMPLE 11

Preparation of the Formula (V) 3-hydroxymethyl-4-phenyl-piperidine in Which R is Benzyl and X is F 5.8 g of the product obtained as described in Example 10 are dissolved in 35 ml of THF and added in 20 minutes to 120 ml of a 1M solution of borane in THF at 5° C. The reaction is maintained for 4 hour at 45° C. 13 ml hydrogen chloride 13% were added in 1 hour maintaining temperature below 10° C. The mixture is heated to reflux and maintained under stirring for 12 hours. After cooling, 20 ml sodium hydroxide 30% are added, the organic layer is separated and concentrated at reduced pressure. 4.16 g 1-benzyl-3-hydroxymethyl-4-p-fluorophenyl-piperidine (yield 89%). For the determination of optical purity of this material, a small part of it has been debenzylated with hydrogen in presence of palladium on carbon and N-methylated with formaldehyde in hydrogen atmosphere and palladium on carbon.

The so obtained N-methyl derivative is analysed by HPLC on Chiralpak AD showing a 65:35 ratio of the (3S,4R) and (3R,4S) isomers.

EXAMPLE 12

Preparation of the Formula (I) 3-[(1.3-benzodioxol-5-yloxi)methyl]-4-phenyl-piperidine in Which R is Benzyl and X is F 2.3 g of the N-benzyl-3-hydroxymethyl-4-(p-fluorophenyl)-piperidine prepared according to Example 11 are dissolved in 8 ml of THF. To this solution 0.9 g of sesamol, 2.4 g of triphenylphosphine and 1.25 ml of diethylazodicarboxylate are added. The mixture is maintained for 15 hours under stirring at room temperature. 8 ml of toluene and 13 ml of water are added, pH is corrected to 4 with hydrogen chloride. The aqueous phase is separated, methylene chloride is added and Sodium hydroxide is added until pH=11 is reached. Phases are separated and solvent is removed from the organic one by evaporation at reduced pressure yielding 3.3 g of N-benzyl-paroxetine as a brown oil.

This product was purified by chromatography on silica gel using THF as eluant obtaining 1.5 g of pure product (yield 45%).

EXAMPLE 13

Preparation of Formula (I) 3-[(1,3-benzodioxol-5-yloxi)methyl]-4-phenyl-piperidine in Which R is H and X is F 1 g of the N-benzyl-3-(1,3-benzodioxol-5-yloxi)methyl)-4-(p-fluorophenyl)-piperidine obtained as described in Example 12 are dissolved in 9 ml of isopropanol and 1 ml of acetic acid. 0.1 g of palladium on carbon are added. The mixture is stirred at 50° C. under hydrogen (5 atm) for 4 hours. After filtration of the catalyst and evaporation of the solvent the product is crystallised from ethyl acetate obtaining 0.75 g of paroxetine acetate (yield 81%).

EXAMPLE 14

Preparation of the Formula (IV) 2-keto-3-carboxyethyl-4-(p-fluorophenyl) 6-hydroxy-piperidine in Which R is Methyl, $R_1$ is Ethyl and X is F To a 100 ml flask containing 12 ml of $CHCl_3$, 1.60 g (10.7 mmol) of p-fluoro cinnamaldehyde prepared as described in Example 8, 1.55 g of the monoamide prepared as described in Example 1, and 2.13 g of (L)-proline rubidium salt are added in an inert atmosphere. It is then stirred for 6 hours at 25° C., the pH is adjusted to pH 5 with a 2N aqueous solution of HCl, the phases are separated, then the solvent is removed from the organic portion at reduced pressure. The residue is purified by chromatography on silica with the mixture methylene chloride:ethyl acetate 95:5 as the eluant.

1.9 g of the title product as a white solid product are obtained (Yield 60%). The $^1$H-NMR spectrum of this product, recorded with a Bruker 200 MHz with $CDCl_3$ as the solvent, is reported in FIG. 1.

EXAMPLE 15

Preparation of the Formula (V) (3S, 4R)-3-hydroxymethyl-4-(p-fluorophenyl)-piperidine in Which R is Methyl and X is F To a suspension obtained with 0.64 g (16.9 mmol) of $LiAlH_4$ and 20 ml of anhydrous THF, cooled to 0° C., is added over 10 minutes a solution of 1 g (3.4 mmol) of the 2-keto-3-carboxyethyl-4-(p-flubrophenyl)-6-hydroxy-piperidine (IV) prepared in Example 14.

After addition the mixture is warmed to 35° C., kept at this temperature and stirred for 4 hours.

After cooling to 0° C., 10 ml of ethyl acetate and then 0.5 ml of methanol and 0.5 ml of water are added over a period of 5 minutes.

After Buchner filtration of the solid, it is concentrated at reduced pressure and chromatography of the residue on silica with the mixture methylene chloride:methanol 95:5 as the eluant is performed.

0.62 g of the product (V) in whoch R is methyl and X is F are obtained (Yield 78%). Chiral column HPLC analysis, according to the method used in Example 3, shows that the isomers (3S,4R) and (3R,4S) are in a ratio of 73:27.

The title (3S,4R) isomer was isolated from this mixture by crystallization as salt with (−)-Di-O-O'-p-toluyl-L-tartaric acid and used in the following step.

EXAMPLE 16

Preparation of (3S,4R)-3-[(1,3-benzodioxol-5-yloxi)methyl]-4-(p-fluorophenyl)-piperidine of Formula (I) in Which R is Methyl and X is F The title compound was prepared according to Example 6 starting from the (3S,4R)-3-hydroxymethyl-4-(p-fluorophenyl)-piperidine (V) obtained as described in Example 15.

EXAMPLE 17

Preparation of (3S, 4R)-3-[(1,3-benzodioxol-5-yloxi)methyl]-4-(p-fluorophenyl)-piperidine of Formula (I) in Which X=F and R=H The title compound (paroxetine) was prepared according to Example 7 starting from the (3S,4R)-3-[(1,3-benzodioxol-5-yloxi)methyl]-4-(p-fluorophenyl)-piperidine (I) obtained as described in Example 16.

EXAMPLE 18

Preparation of the Formula (I) 3-[(1,3-benzodioxol-5-yloxi)methyl]-4-(p-fluorophenyl)-piperidine in Which R is H and X is F In a reactor, at room temperature and in succession, are put 1 g (4.9 mmol) of 3-hydroxymethyl-4-(p-fluorophenyl)-piperidine, 0.66 g (4.8 mmol) of sesamol, and 1.75 g of triphenylphosphine.

8 ml of toluene are then added, and the reaction mixture is put under stirring.

Then 1.1 ml of diethyl azodicarboxylate are added over 5 minutes, dissolving the suspended solid during addition.

20 ml of methanol are added after 12 hours and the solution is still stirred for a further 30 minutes. Afterwards the solvent is removed at reduced pressure, obtaining 4.88 g of raw product which is purified by chromatography using silica as the stationary phase and the mixture ethyl acetate: methanol : aqueous ammonia 8:2:0.5 as the eluant.

In this way 1.37 g of paroxetine are obtained (Yield 87%).

EXAMPLE 19

Preparation of the Formula (V) 3-hydroxymethyl-4-(p-fluorophenyl)-piperidine in Which R is Methyl and X is F In an anhydrous flask to 16.1 g sodium borohydride a solution in 250 ml THF of 25 g of the hydroxylactam (IV) prepared as described in Example 14, is added. 11.5 ml sulfuric acid 96% are added in 3 hours. The mixture is heated to 45° C. and maintained under stirring for 2 hours. Reaction is stopped by addition of 42 ml hydrogen chloride 20% at 5° C., the mixture is heated to reflux and maintained for 8 hours. 120 ml sodium hydroxide 18% are added at room temperature, after stirring, phases are separated. Solvent is removed from the organic phase by distillation at reduced pressure and the product (20.6 g) is used in the following step without further purification. (yield 67% calculated by HPLC vs external standard).

EXAMPLE 20

Preparation of the Formula (V)3-hydroxymethyl-4-(p-fluorophenyl)-piperidine in Which R is Methyl and X is F The preparation as described in Example 19 is conduced again with the only difference that 11 ml of methanesulfonic acid are used instead of 11.5 ml sulfuric acid 96%. In this case the yield is 68%.

EXAMPLE 21

Preparation of the Formula (V) 3-hydroxymethyl-4-(D-fluorophenyl)-piperidine in Which R is Methyl and X is F 5 g of the hydroxylactam prepared as described in Example 14 are dissolved in 35 ml of THF. The resulting solution was added drop by drop to a 1M solution of borane in THF while temperature was kept at 0/5° C. The temperature was increased to 45° and stirring maintained for 4 hours. After having cooled to 5° C., 15 ml of a 33% aqueous solution of HCl are added in 20 minutes, the mixture heated to 600° C., and maintained at this temperature for 15 hours under stirring. The organic phase is then separated and concentrated under reduced pressure to afford the piperidine derivative of the title (Yield 70%).

EXAMPLE 22

Preparation of the Formula (IV) 2-keto-3-carboxyalkyl-4-phenyl-6-hydroxy-piperidine in Which R is Benzyl, $R_1$ is Ethyl and X is F According to the procedure described in Example 2 the title compound was prepared using the formula (III) amide in which R is benzyl prepared as described in Example 9.

EXAMPLE 23

Preparation of the 3-hydroxymethyl-4-phenyl-piperidine of formula (V) in Which R is Benzyl and X is H The title compound was prepared according to Example 3 starting from 2-keto-3-carboxyethyl-4-phenyl-6-hydroxy-piperidine of formula (IV) obtained as described in Example 22.

EXAMPLE 24

Preparation of the Formula (I) 3-[1,3-benzodioxol-5-yloxi)methyl]-4-phenyl-piperidine in Which R is Benzyl and X is H The title compound was prepared according to Example 6 starting from 3-hydroxymethyl-4-phenyl-piperidine (V) obtained as described in Example 23.

EXAMPLE 25

Preparation of the Formula (I) 3-[1,3-benzodioxol-5-yloxi)methyl]-4-phenyl-piperidine in Which R=X=H In a flask 10 9 of 3-[1,3-benzodioxol-5-yloxi)methyl]-4-phenyl-piperidine (I) obtained as described in Example 24 are dissolved in 70 ml of ethanol. To this solution are added 5 ml of acetic acid and 2 g of Pd/C. The hydrogenation is then carried out with $H_2$ at 10 atm at a temperature of 65° C. for 3 hours.

The catalyst is removed by filtration and the solvent is evaporated at reduced pressure, obtaining a residue that is suspended in 200 ml of ethyl acetate. After having concentrated it at reduced pressure, 100 ml of ethyl acetate and 1.6 g of acetic acid are added, then cooled to 0° C. and 5.1 g of desfluoro paroxetine acetate are obtained by filtration (yield=53.3%).

EXAMPLE 26

Preparation of the Amide of Formula (III) in Which R is Methyl and $R_1$ is Isopropyl 1.4 g sodium hydride (60% in mineral oil) are added to a solution prepared by dissolving 101.5 g of 2-carboethoxy-N-methyl-acetamide in 1 l of isopropanol. The reaction is maintained at room temperature for 5 hours. The mixture is neutralised with acetic acid, then the solvent is removed at reduced pressure, and the product is isolated by distillation at 6 mmHg (Teb 115° C.). 91.4 g of 2-carboisopropoxy-N-methyl-acetamide are obtained (yield 82%).

EXAMPLE 27

Preparation of the 2-keto-3-carboxyalkyl-4-phenyl-6-hydroxy-piperidine of Formula (IV) in Which R is Methyl, $R_1$ is Isopropyl and X is F A solution is prepared by dissolving 7.86 g of the 2-carboisopropoxy-N-methyl-acetamide obtained as described in Example 26 and 8.36 g of p-fluorocinnamaldehyde prepared as described in Example 8, in 46 ml toluene, and heated to 70° C. To this solution a solution of 0.305 g L-proline and 0.29 ml rubidium hydroxide 50% in water is added under stirring in 20 minutes. Temperature and stirring are maintained for 3 hours, then 15 ml of water are added. After phase separation, the solvent is removed at reduced pressure.

The residue (17.9. g) is purified by chromatography on silica gel with the mixture methylene chloride: ethyl acetate 95: 5 as the eluant. The collected fractions containing the product are unified and dried yielding 12.1 g of 1-methyl-2-keto-carboxyisopropyl-4-(p-fluorophenyl)-6-hydroxy-piperidine (yield 70%).

EXAMPLE 28

Preparation of the (3S. 4R)-3-hydroxymethyl-4-phenyl-piperidine of Formula (V) in Which R is Methyl and X is F 12 g of 1-methyl-2-keto-carboxyisopropyl-4-(p-fluorophenyl)6-hydroxy-piperidine obtained as described in Example 27 are dissolved in 30 ml of THF. To this solution are added under stirring in 10 minutes at 5° C., 210 ml of a 1M borane solution in THF. Temperature is brought up to 45° C., and stirring is maintained for 4 hours.

30 ml of a 15% HCl aqueous solution are added, and the mixture is heated to 60° C. maintaining this temperature for 12 hours. After having cooled the reaction mixture to room temperature, a 30% aqueous solution of sodium hydroxide is added until pH 12 is reached. The organic phase is separated and concentrated under vacuum. HPLC analysis on Chiralpak AD column of the so obtained residue shows that the relative amounts of (3S,4R) and (3R,4S) isomers is 68:32.

This residue is dissolved in 15 ml acetone, and 2 g of (−)-di-O,O'-p-toluyl-L-tartaric acid in 13 ml of acetone are added.

Mixture is heated to 55° C., then cooled at 10° C. The product is collected by filtration, and dissolved in 50 ml of water and 50 ml of toluene. Sodium hydroxide is added until pH=12 is reached; the organic phase is separated, and the solvent is removed at reduced pressure, obtaining 3 g of 1-methyl-3-hydroxymethyl-4-(p-fluorophenyl)-piperidine (yield 35%). The chiral HPLC analysis of this product shows that its enantiomeric purity is higher than 99%.

What is claimed is:

1. A process for the preparation of 3-substituted 4-phenyl-piperidine derivatives of formula(I)

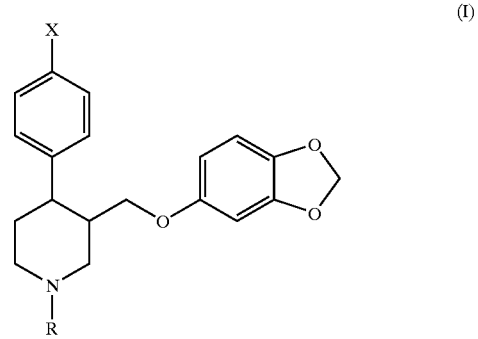

In which X is selected from H and F, and R is selected from the group consisting of H, C1–C6 alkyl, C3–C6 alkenyl, and benzyl, comprising the following steps:

a) Michael addition between the formula (II) cinnamic aldehyde and the amide of formula (III) in which $R_1$ is selected from the group consisting of C1–C6 alkyl, C3–C6 alkenyl, and benzyl, to obtain the formula (IV) 2-keto-3-carboxyalkyl-4-phenyl-6-hydroxy-piperidine, optionally enriched in the (3S,4R) isomer by using a suitable chiral catalyst:

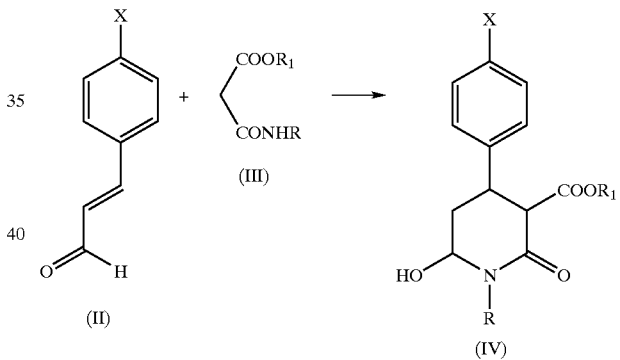

b) reduction of the formula (IV) 2-keto-3-carboxyalkyl-4-phenyl-6-hydroxy-piperidine coming from step a) to obtain the 3-hydroxymethyl-4-phenyl-piperidine of formula (V):

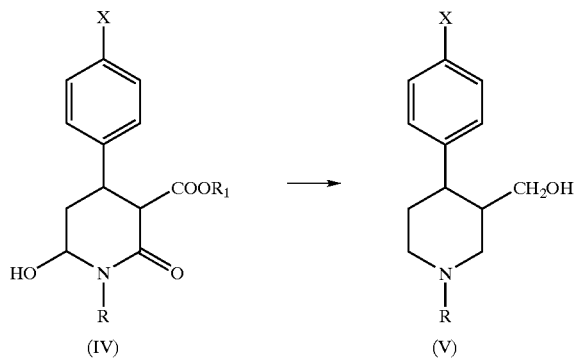

c) reaction of 3-hydroxymethyl-4-phenyl-piperidine of formula (V) coming from step b) with sesamol (VI) to obtain the formula (I) 3-[(1,3-benzodioxol-5-yloxoli)methyl]-4-phenyl-piperidine:

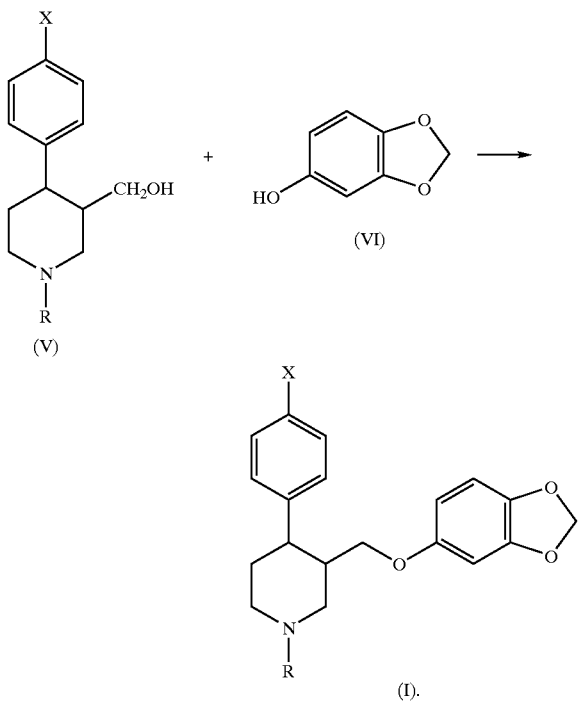

2. The process according to claim 1, in which, when in the said 3-hydroxymethyl4-phenyl-piperidine of formula (V) coming from step b) R≠H, between step b) and step c) a further step is carried out, of hydrogenation when R is benzyl, of dealkylation when R is alkyl, and of deallylation when R is alkenyl.

3. The process according to claim 1, wherein said chiral catalyst in step a) is a salt of (L)-proline, said salt of (L)-proline is selected from (L)-proline potassium salt and (L)-proline rubidium salt.

4. The process according to claim 1, wherein in the said addition of step a) the molar ratio between the (L)-proline salt and cinnamaldehyde (II) ranges between 0.05:1 and 1:1.

5. The process according to claim 1, wherein the said reduction in step b) is carried out with a metallic hydride.

6. The process according to claim 1, wherein the said reduction in step b) is carried out with lithium aluminum hydride or with sodium borohydride in combination with aluminum chloride or in combination with hydrochloric acid.

7. The process according to claim 1, in which the said step c) is carried out with triphenylphosphine and diethyl azodicarboxylate.

8. Compound according to formula (IV)

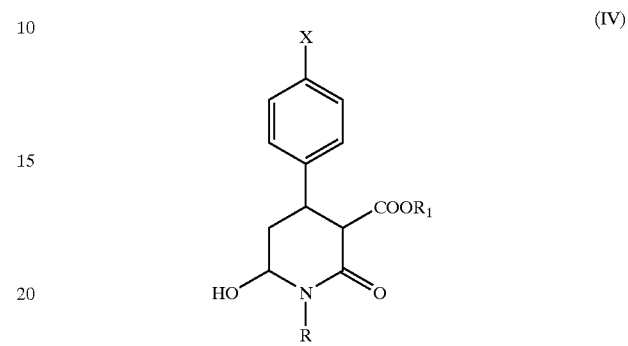

in which $R_1$ is selected from the group consisting of C1–C6 alkyl, C3–C6 alkenyl, and benzyl, X is selected from H and F, and R is selected from the group consisting of H, C1–C6 alkyl, C3–C6 alkenyl, and benzyl.

9. Compound of formula (IV')

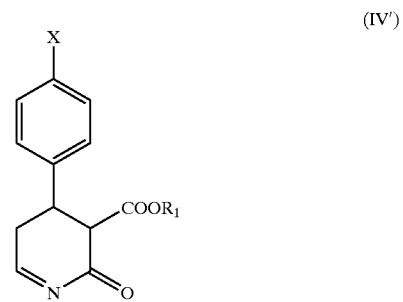

in which $R_1$ is selected from the group consisting of C1–C6 alkyl, C3–C6 alkenyl, and benzyl, and X is selected from H and F.

* * * * *